(12) United States Patent
Shimizu

(10) Patent No.: US 7,084,082 B1
(45) Date of Patent: Aug. 1, 2006

(54) COLLAGEN MATERIAL AND ITS PRODUCTION PROCESS

(75) Inventor: Yasuhiko Shimizu, Uji (JP)

(73) Assignee: Tapic International Co., Ltd., Tokyo (JP)

( * ) Notice: Subject to any disclaimer, the term of this patent is extended or adjusted under 35 U.S.C. 154(b) by 0 days.

(21) Appl. No.: 09/719,316

(22) PCT Filed: Jun. 7, 1999

(86) PCT No.: PCT/JP99/03019

§ 371 (c)(1),
(2), (4) Date: Dec. 11, 2000

(87) PCT Pub. No.: WO99/64655

PCT Pub. Date: Dec. 16, 1999

(30) Foreign Application Priority Data

Jun. 11, 1998 (JP) .................................. 10-163674
Jul. 16, 1998 (JP) .................................. 10-201405

(51) Int. Cl.
*A61F 2/02* (2006.01)
*B32B 5/02* (2006.01)

(52) U.S. Cl. ........................ 442/123; 424/443; 424/444; 442/334; 442/340; 514/801; 604/367; 604/368; 623/915; 623/917

(58) Field of Classification Search ................ 424/444, 424/443; 602/151, 154; 106/122; 604/368; 606/229, 154, 151; 514/801; 530/356; 428/296.7
See application file for complete search history.

(56) References Cited

U.S. PATENT DOCUMENTS 6,179,872 B1 * 1/2001 Bell et al. ................ 623/11.11

FOREIGN PATENT DOCUMENTS

WO      WO 9822157 A1 * 5/1998

* cited by examiner

*Primary Examiner*—Ula Ruddock
*Assistant Examiner*—Jennifer Boyd
(74) *Attorney, Agent, or Firm*—Edwards Angell Palmer & Dodge, LLP; David G. Conlin; Mark D. Russett

(57) ABSTRACT

The objective of the present invention is to provide a collagen material that possesses physical properties to an extent that allows suturing while still maintaining the biochemical properties inherently possessed by collagen, and retains its shape for a certain amount of time even after application to the body; its production process; and, a medical material on which it is based, examples of which include a artificial tube for nerve, artificial tube for spinal cord, artificial esophagus, artificial trachea, artificial blood vessel, artificial valve or alternative medical membranes such as artificial endocranium, artificial ligaments, artificial tendons, surgical sutures, surgical prostheses, surgical reinforcement, wound protecting materials, artificial skin and artificial cornea, characterized by filling or having inside a substance having biocompatibility that can be degraded and absorbed in the body into a matrix of a non-woven fabric-like multi-element structure of collagen fibers having ultrafine fibers of collagen as its basic unit.

25 Claims, 1 Drawing Sheet

COLLAGEN MATERIAL AND ITS PRODUCTION PROCESS

TECHNICAL FIELD

The present invention relates to a collagen material comprising a substance having biocompatibility that can be degraded and absorbed in the body in a matrix of a collagen ultra-fine fibrous non-woven fabric-like multi-layer structure, or in a non-woven fabric-like matrix of a substance having biocompatibility that can be degraded and absorbed in the body, a material of a specific form containing said collagen material, a medical material comprised of said material, and their production processes.

BACKGROUND ART

Among the various materials used as medical materials, animal collagen has excellent bioaffinity and histocompatibility, low antigenicity, has the action of promoting host cell differentiation and growth, has a hemostatic action, and is completely degraded and absorbed in the body. Consequently, it has properties that are particularly suitable for use as a medical material. At present, animal collagen types I through XIX have been discovered, collagen types I through V are used in a variety of ways as medical materials. In particular, type I collagen, which is useful as an extracellular matrix, is used most commonly. These collagens are extracted and purified from the connective tissue of various organs such as skin, bone, cartilage, tendon, and viscus of animals such as cows, pigs, birds, kangaroos and so forth by acidic solubilization, alkaline solubilization, neutral solubilization and enzymatic solubilization. Extracted collagen used conventionally is one that has been broken down to monomers and oligomers at the molecular level, and is stored in the form of a powder or liquid. Since these extracted collagens are in a state in which collagen molecules are broken down to monomers and oligomers, when they come in contact with water, body fluids or blood, they form a sol extremely rapidly. Consequently, when using these collagens by forming as medical materials, they are either used by covering the surface of a synthetic polymer material such as Nylon or silicone with collagen to give the material a certain degree of strength during processing, or are used by subjecting the formed product of the extracted collagen to chemical crosslinking treatment using a crosslinking agent or to physical crosslinking treatment using radiation, electron beam, ultraviolet rays or heat in order to hold the shape of the material for a certain period of time in the case of applying to the body. In addition, although these extracted collagens may be used as thread for medical treatment by forming into the shape of a thread, wet spinning is used for its spinning.

However, in the case of a material in which collagen is combined with a synthetic polymer material, the synthetic polymer material remains in the body as a foreign object resulting susceptibility to the occurrence of disorders such as granulation and inflammation, and this type of material cannot be applied to all cells and viscera. In addition, even if crosslinking treatment is performed on collagen materials, since there is hardly any increase at all in the physical properties of the collagen material, and particularly tear strength, it was not possible to process this material for use as a medical material requiring suturing. In addition, when a crosslinking agent such as glutaraldehyde or epoxy is used, not only does the toxicity of the crosslinking agent on the body become a problem, but there is also the disadvantage of the biochemical properties inherently possessed by collagen, and particularly promotional effects on cell growth, being lost. In addition, in the case of physical crosslinking treatment, the crosslinking rate is unstable and it is unable to give adequate physical properties to the collagen material. In addition, it has also been difficult to perform crosslinking treatment so that the absorption rate in the body can be controlled. On the other hand, since spun collagen does not have sufficient strength, it is not adequate for use as suture.

On the other hand, although it is necessary to close by resuturing an opened endocranium, pericardium, pleura, peritoneum or serous membrane when closing a surgical wound after performing surgery on the brain or various viscera for the treatment of various diseases or trauma, there are many cases in which a missing portion forms in the membrane that prevents a surgical wound from being completely closed due to the formation of a shortened portion depending on the length of the suture or the membrane being partially severed. If such a missing portion is left uncorrected, the viscera such as the brain, heart, lung and intestine may herniate from the area where the membrane is missing resulting in a serious disorder, or water or air may escape from the viscera or area around the viscera preventing the surgical wound from healing. In addition, since the viscera may adhere to surrounding tissues, the tissue may be damaged thereby preventing the obtaining of a favorable prognosis. Consequently, freeze-dried human endocranium removed cadavers or porous elastic polytetrafluoroethylene (EPTFE) (Tissue Goretex, trade name), polypropylene mesh, Teflon sheet or Dacron sheet and so forth are used as alternative medical membranes that can be used as prostheses for these missing portions. In addition, a copolymer of lactic acid and $\epsilon$-caprolactone (50:50) is currently being developed. In addition, methods involving the use of the patient's own fascia lata, pericardium, skin or muscle and so forth are also performed as a last resort.

However, with respect to the use of human endocranium, adhesion occurs between the filled human endocranium and brain parenchymal tissue. Not only does this have the risk of causing epileptic attacks following surgery, there is also the ethical problem of obtaining specimens from human cadavers as well as the problem of the supply being extremely limited. More recently, the occurrence of Creutzfeldt-Jakob Disease (CJD) caused by transplanted endocranium has been reported in patients receiving endocranial transplants (J. Neurosurgery, 21(2): 167–170, 1993). In Japan, human endocranium is currently not used. In addition, since EPTFE materials and so forth are not degraded in the body but rather remain as foreign objects, they easily cause infection or, when in contact with body tissue, end up causing fatty degeneration of tissue cells and so forth, and are known to frequently cause post-operative complications. Copolymers of lactic acid and E-caprolactone are degradable in the body. Although they gradually are degraded after being applied to the body, a long period of time on the order of nearly two years is required for them to be completely degraded and absorbed. Consequently, they also remain in the body for the time being as foreign objects, cause inflammation in tissue during the degradation process and form granuloma. Since this copolymer uses the (L) form of lactic acid as its monomer, lactic acid may crystallize in the copolymer causing inflammation. Moreover, both EPTFE and copolymer of lactic acid and $\epsilon$-caprolactone do not have the action of promoting regeneration of biomembranes. In addition, methods using the patient's own fascia lata and so forth place a significant burden on both the patient and physician.

Although materials such as the above-mentioned EPTFE, polypropylene mesh (Marlex), human dried endocranium and glutaraldehyde (GA)-treated bovine pericardium have been used in the past as pericardium prostheses, EPTFE and human dried endocranium have the disadvantages described above. In addition, polypropylene mesh causes strong adhesion between itself and the heart. Since GA-treated bovine pericardium remains in the body without being absorbed or degraded, it causes deterioration due to mineral deposition, and complications due to interstitial pneumonia caused by an immune reaction to the bovine pericardium have also been observed.

In addition, although polyglycolic acid non-woven fabric and bovine pericardium have been used as a pleural prosthesis or for an auto-suture to reduce the escape of air from the surgical site following lung surgery, because polyglycolic acid is not transparent, it is difficult to be used for an auto-suture. In addition, bovine pericardium has the disadvantages previously described.

DISCLOSURE OF THE INVENTION

For these reasons, a need has arisen for the development of a collagen material that possesses physical properties to an extent that allows suturing while still maintaining the biochemical properties inherently possessed by collagen, and retains its shape for a certain amount of time even after application to the body; its production process; and, a medical material on which it is based, examples of which include a artificial tube for nerve, artificial tube for spinal cord, artificial esophagus, artificial trachea, artificial blood vessel, artificial valve or alternative medical membranes such as artificial endocranium, artificial ligamenta, artificial tendons, surgical sutures, surgical prostheses, surgical reinforcement, wound protecting materials, artificial skin and artificial cornea. In particular, there has arisen a strong need in the clinical setting for the development of various types of medical materials that can be used as alternative medical membranes which present no ethical problems, are in stable supply, prevent adhesion of the surgical wound following surgery after being applied to the body, have no risk of infection, do not cause tissue degeneration, allow control of the rate of degradation following application, and have an action that promotes regeneration of biomembranes, especially endocranium, pericardium, pleura, peritoneum or serous membrane.

As a result of earnest research to solve the above-mentioned problems, the inventors of the present invention found that a collagen material comprising filling or having inside a substance having biocompatibility that can be degraded and absorbed in the body into a matrix of a non-woven fabric-like multi-element structure having ultra-fine fibers of collagen for its basic unit, or a collagen material comprising filling a substance having biocompatibility that can be degraded and absorbed in the body into a non-woven fabric-like matrix of a substance having biocompatibility that can be degraded and absorbed in the body, has excellent properties as a medical material as well as physical properties that allow suturing, thereby leading to completion of the present invention.

Namely, the present invention is a collagen material characterized by filling or having inside a substance having biocompatibility that can be degraded and absorbed in the body into a matrix of a non-woven fabric-like multi-element structure of collagen fibers having ultra-fine fibers of collagen as its basic unit.

The collagen material of the present invention has the basic structure as shown in FIG. 1, and the matrix of non-woven fabric-like multi-element structure of collagen fibers that takes its leading part is composed pluralistically from various types of fibrous collagen of different sizes and shapes as explained below.

Namely, the non-woven fabric-like multi-element structure of collagen fibers has for its basic unit ultra-fine fibers 15 comprised of several collagen molecules and having a diameter of 3–7 nm, said ultra-fine fibers are bundled to form fine fibers 14 having a diameter of 30–70 nm, and said fine fibers are further bundled to form narrow fibers 13a and 13b having a diameter of 1–3 μm. Next, bundled rows of said narrow fibers form fibers 12 having a diameter of 5–8 μm by alternatively overlapping as warp and weft, and said fibers overlap in the coaxial direction to form plate-like fibers 11 having a diameter of 20–50 μm. Finally, these plate-like fibers 11 randomly intertwine to form fibrous collagen as the largest unit in collagen ultra-fine fibrous non-woven fabric-like multi-layer structure 10.

The collagen material of the present invention contains a substance having biocompatibility that can be degraded and absorbed in the body in a matrix of a multi-element structure of fibrous collagen in which plate-like fibers 11 are gathered in the form of a non-woven fabric. Here, a typical example of a substance having biocompatibility as well as biodegradability and bioabsorption are collagen fibers containing ultra-fine fibers of collagen newly formed in said matrix by subjecting a hydrochloric acid solution of extracted collagen introduced into said matrix to freezing and freeze-drying treatment. However, other examples of candidates for this substance include that in which a solution of said extracted collagen or hyaluronic acid solution is introduced into said matrix followed by air drying said solution (and that originating in collagen is to be referred to as amorphous collagen).

Moreover, the collagen material of the present invention may also have an additional layer comprising an air-dried solution of extracted collagen at a predetermined site on the surface of the above collagen material.

In addition, although the collagen material of the present invention has the basic structure as shown in FIG. 1, depending on the application of said material, it may also have a mesh-like intermediate material in the form of a sheet or tube comprising a biodegradable, absorbable material inside the above non-woven fabric-like multi-element structure of collagen fibers.

Moreover, in the collagen material of the present invention, the above matrix may be in the form of a non-woven fabric-like sheet or tube comprising a substance having biocompatibility that can be degraded and absorbed in the body, examples of which include a material selected from the group consisting of polyglycolic acid, polylactic acid, copolymers of glycolic acid and lactic acid, polydioxanone, copolymers of glycolic acid and trimethylene carbonate, or mixtures of polyglycolic acid and polylactic acid, and the substance having biocompatibility that can be degraded and absorbed in the body which is filled into said matrix may be collagen (collagen fiber or amorphous collagen) or hyaluronic acid similar to that filled into the above matrix.

This collagen material of the present invention can be produced by a process comprised of the steps indicated below.

(Basic Process)

Step a

A hydrochloric acid solution of extracted collagen is cast to the desired thickness to form a collagen solution layer. Here, casting should be performed by suitably selecting a known method according to the target shape of the collagen material. For example, in the case of seeking a film-like collagen material, casting should be performed using a vat and so forth for the mold, while in the case of seeking a tubular collagen material, casting should be performed using a mold having a cavity at the portion corresponding to the wall of the object (and this applies similarly hereinafter).

Step b

Said collagen solution layer is temporarily frozen, and after holding for the desired amount of time in that state, said collagen solution layer is freeze-dried. At this point, a multi-element structure of collagen fibers having collagen ultra-fine fibers as its basic unit is formed. However, since said multi-element structure of collagen fibers is in the form of a matrix, a large number of cavities therein, referring to spaces, but not so-called pores, in which solution is able to penetrate, are present in that matrix.

Step c

Thermal dehydration crosslinking is then performed on said freeze-dried product (to impart a predetermined stability to water to the fibrous collagen composing a matrix in the next step).

Step d

A hydrochloric acid solution of extracted collagen is introduced into the matrix of the product suffered said thermal dehydration crosslinking treatment. As a result, the cavities in said matrix are filled with non-fibrous collagen. Here, it is not necessary that the cavities filled in this procedure account for the entire volume of the cavities in said matrix. Furthermore, a specific example of an introduction method is a method involving aspirating with a weak vacuum. Naturally, the method used is not limited to this method provided solution can be effectively introduced into minute cavities.

Step e

The product introduced said extracted collagen is again frozen, held in that state for a desired amount of time, and then freeze-dried. In this procedure, at least a portion of the cavities in the above matrix are filled with collagen fibers containing ultra-fine fibers of newly formed collagen. Here, "filled" refers, more accurately, to collagen fibers containing ultra-fine fibers of collagen newly formed in the cavities of said matrix being present so as to intertwine with each fibrous collagen fiber that composes said matrix.

Step g

Said freeze-dried product is compressed.

Step i

Thermal dehydration crosslinking is then performed on said compressed product. In this procedure, the predetermined stability to water is imparted to collagen fibers containing ultra-fine fibers of newly formed collagen, in the final product or in an additional step performed as a variation of the production process.

Moreover, the following steps may be performed in order between the above steps e and g. (It is preferable to fill said cavities as much as possible to obtain the desired strength, as much as is allowed by properties such as "feeling" and "flexibility" other than the strength required by the finished collagen material, with collagen fibers containing ultra-fine fibers of newly formed collagen in the cavities of the above matrix. In this connection, the volume ratio of said cavities expressed as the percentage of void is typically 50–60% in the state of the matrix, about 10% after step e, and about 5% after step e after repeating one cycle of step d and step e, and it is sufficient to perform one cycle of step f1 and step f2 as described below in the case of normal applications of said collagen material, such as an alternative medical membrane.

Step f1

A hydrochloric acid solution of said extracted collagen is introduced into the matrix of the above product of freeze-drying.

Step f2

After introducing said hydrochloric acid solution of extracted collagen, the product is again frozen temporarily, held in that state for a desired amount of time, and then freeze-dried.

In addition, the following steps may be performed between the above steps g and i.

Step h1

A collagen solution layer is formed at a predetermined site on the surface of the above compressed product. More specifically, said compressed product should be immersed and air-dried at least once for a predetermined amount of time in a hydrochloric acid solution of extracted collagen, preferably having a collagen concentration of 2.0% or less. This is done in the case of intending to use the collagen material in an application in which the decrease in strength resulting from infiltration of body fluids from said site is desired to be suppressed as much as possible. Furthermore, during the formation of a collagen solution layer at a "predetermined site", those portions not requiring the formation of said collagen solution layer should be blocked with a suitable known means during immersion of the extracted collagen in the hydrochloric acid solution.

In the case of performing step h1, step h2 as described below, namely the procedure of "compressing the above collagen layer again", may be performed prior to performing the next step in the form of step i (in the case of desiring to eliminate or reduce surface irregularities in the collagen material and improve "feeling" and "texture").

Furthermore, in the case of using that into which hydrochloric acid solution of extracted collagen or hyaluronic acid solution (in which case "hydrochloric acid solution of extracted collagen" in the above step d should be read as "hyaluronic acid solution") is introduced into said matrix and air-dried for the substance filled into the above matrix, the procedures of steps e to i may be omitted, and said matrix should be subjected to thermal dehydration crosslinking for a predetermined amount of time while pressing the matrix into which the above hydrochloric acid solution of extracted collagen or hyaluronic acid solution has been introduced. Here, pressing of said matrix is performed to minimize the effects of air remaining in said matrix, or in other words, to minimize the occurrence of local "bulging" of the collagen material.

On the other hand, in the case of using a material selected from the group consisting of polyglycolic acid, polylactic acid, copolymers of glycolic acid and lactic acid, polydioxanone, copolymers of glycolic acid and trimethylene carbonate and mixtures of polyglycolic acid and polylactic acid (to be referred to as polyglycolic acid, etc.) for the substance having biocompatibility and able to be degraded in the body that is placed inside the above matrix, in the above step a, casting of hydrochloric acid solution of extracted collagen is performed by dividing into two cycles, and a mesh-like material in the form of a sheet or tube comprised of the above material should simply be contained inside between both casting procedures (and more specifically, said material should be placed over the collagen solution layer cast during the first cycle in the case of obtaining a membrane-like material). Furthermore, since these materials are poorly hydrophilic, it is preferable to modify the surface with plasma and so forth immediately before containing inside.

Furthermore, in the case of having these materials inside said matrix, additional reinforcement of the collagen fibers containing ultra-fine fibers of newly formed collagen in said matrix is not required as a general rule in order to obtain a predetermined strength with the compounding effects of these materials and the matrix (system constitution: partially altered step a→step b→step c→step g). However, it is preferable to form a collagen solution layer or gelatin solution layer in the sense of regulating the biochemical condition of the pressed surface.

In addition, in the case of the collagen material of the present invention being that in which the above matrix is in the form of a non-woven fabric-like sheet or tube comprising a substance having biocompatibility that can be degraded and absorbed in the body, for example a material selected from the group consisting of polyglycolic acid, polylactic acid, copolymer of glycolic acid and lactic acid, polydioxanone, copolymer of glycolic acid and trimethylene carbonate or a mixture of polyglycolic acid and polylactic acid, and the substance having biocompatibility that is degraded and absorbed in the body which is filled into said matrix is collagen (collagen fiber or amorphous collagen) or hyaluronic acid similar to that filled into the above matrix, it should be produced as indicated below. Furthermore, for the sake of convenience in the explanation, an explanation is provided using the example of the case of the substance introduced into said matrix being collagen, and the produced collagen material being in the form of a membrane.

Step j

A hydrochloric acid solution of extracted collagen is introduced into a matrix comprising a non-woven fabric-like sheet composed of a material selected from the group consisting of polyglycolic acid, polylactic acid, copolymer of glycolic acid and lactic acid, polydioxanone, copolymer of glycolic acid and trimethylene carbonate or a mixture of polyglycolic acid and polylactic acid, followed by air-drying. This procedure for introducing a hydrochloric acid solution of extracted collagen is performed by placing a hydrochloric acid solution of extracted collagen of a predetermined concentration, in which said matrix is immersed (by placing in a separate container), in a container placed in a slightly depressurized environment, for example, an atmosphere at a pressure somewhat lower than atmospheric pressure from which the air has been removed with a flow aspirator and so forth, and holding in that state for a predetermined amount of time. More specifically, this is performed by allowing said hydrochloric acid solution of extracted collagen to seep into said matrix. Furthermore, as is clear from this procedure, a thin layer composed of said hydrochloric acid solution of extracted collagen is inevitably formed not only inside said matrix but on its surface as well.

Step l

A collagen solution layer is formed on at least one side of the product of introducing said hydrochloric acid solution of extracted collagen and air-drying. More specifically, the product of introducing and air-drying said hydrochloric acid solution of extracted collagen should be immersed in a hydrochloric acid solution of extracted collagen and air-dried in the same manner as above. This should preferably be repeated one to five times. The resulting material is a collagen solution layer. Furthermore, this step should also be performed in which the other side is blocked with a suitable means in order to form this collagen solution layer on only one side.

Step o

A gelatin solution layer is formed on said collagen solution layer. More specifically, coating of an aqueous gelatin solution of a predetermined concentration or immersion in said aqueous gelatin solution should be performed. Furthermore, this step is an arbitrary step that is required in the case of requiring the final product to have the ability to prevent adhesion.

Step p

Thermal dehydration crosslinking is performed for a predetermined amount of time on that product on which said gelatin solution layer is formed. The objective of this step is to impart stability to water in the same manner as that imparted to the collagen fibers and so forth in the previously described method.

Although the process thus far constitutes the basic steps in this method, there are variations to this method. In one of these variations, fiber formation from collagen solution is respectively performed between steps j and l and between steps l and o. More specifically, a series of procedures consisting of freezing followed by holding followed by freeze-drying is added to the extracted collagen and collagen solution layer introduced into the matrix in the same manner as the previously described method (that with respect to the former being referred to as additional step k, and that with respect to the latter being referred to as additional step m1). Furthermore, these additional steps are employed in the case that the strength of the matrix used as a strength exhibiting member is weak (and more specifically, when the thickness of the non-woven fabric-like matrix is thin). Here, it is preferable that the product of said freeze-drying be pressed following additional step m1 (additional step m2). This is done to increase overall strength.

Thermal dehydration crosslinking is another example of an additional step. This additional step is performed between step l and step o or between step m2 and step o (additional step n that is performed for the purpose of imparting stability to water to the product in the same manner as that described in the previous method).

Although the collagen material of the present invention can be used as the main constituent material of medical materials such as artificial tube for nerve, artificial tube for spinal cord, artificial esophagus, artificial trachea, artificial blood vessel, artificial valve, artificial ligaments, artificial tendons, surgical prostheses, surgical reinforcement, wound protecting materials and artificial skin, it can be used as is in nearly all cases. Moreover, it is also preferable for artificial medical alternative membrane applications for which there is a considerable need, examples of which include biomembranes, and especially endocranium, pericardium, pleura, peritoneum, serous membrane or cornea.

Furthermore, in the case of membrane-like materials such as surgical prostheses, surgical reinforcement and wound protecting materials, the collagen material of the present invention may have a crosslinked gelatin gel layer or hyaluronic acid layer on one or both sides thereof.

Moreover, the collagen material of the present invention can also be used as a thread-like material and medical material comprising said thread-like material, an example of which is surgical suture. Said thread-like material can be produced using a procedure similar to that for other materials with the exception of performing a procedure that first allows the obtaining of collagen thread by performing wet spinning instead of forming a collagen solution layer in the above step a.

Figure 1:
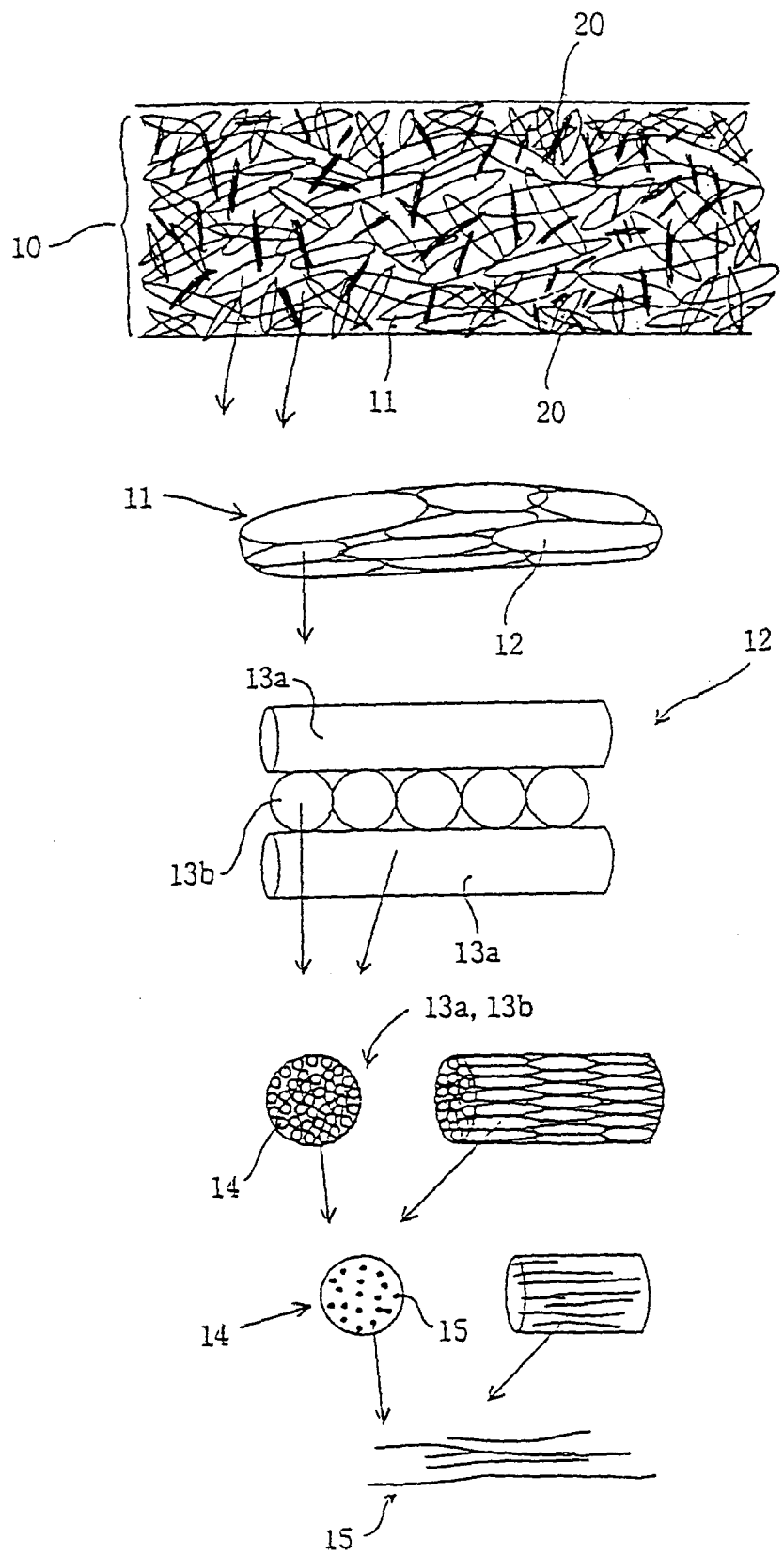
FIG. 1 shows the structure of the collagen material of the present invention.

The following reference numerals are used in the drawing.
10: Collagen ultra-fine fibrous non-woven fabric-like multi-layer structure
11: Plate-like fibers
12: Fibers
13a, 13b: Narrow fibers
14: Fine fibers
15: Ultra-fine fibers
20: Newly formed fibrous collagen

BEST MODE FOR CARRYING OUT THE INVENTION

Examples of collagen that can be used as the raw material of the collagen material of the present invention include various types of collagen conventionally used, and preferably neutral solubilized collagen, acidic solubilized collagen, alkaline solubilized collagen or enzymatic solubilized collagen. Among these, enzymatic solubilized collagen is particularly preferable since it involves treatment of insoluble collagen with enzyme (e.g., pepsin, trypsin, chymotrypsin, papain and pronase), causing the strongly antigenic telopeptide portion in the collagen molecules to be removed by this treatment, resulting in decreased antigenicity. There are no particular restrictions on the origin of this collagen, and in general, type I collagen or mixed type I and type III collagen can be used which is obtained by extraction and purification from the skin, bone, cartilage, tendon, viscera and so forth of animals such as cows, pigs, rabbits, sheep, kangaroos, birds and fish, etc.

When the collagen material of the present invention having a non-woven fabric-like multi-element structure of collagen fibers having ultra-fine fibers of collagen as its basic unit as described above for the matrix is compared with a material comprised only of non-fibrous collagen having an amorphous structure in which collagen molecules are dispersed in the state of monomers and oligomers that have been used in the past as various types of medical materials, in addition that the former retains the action on the body inherently possessed by collagen, in comparison with the latter, not only does it have excellent physical properties, and particularly excellent tear strength, but the rate of absorption in the body is also adequately extended. In addition, with the exception of being in the form of a thread, a thread-like material containing the collagen material of the present invention has the same structure as that described above. In addition, a medical material comprising the collagen material of the present invention is a product of a similar collagen material comprising filling a substance having biocompatibility that is degraded and absorbed in the body into a matrix processed into various types of medical materials. Examples of the forms of medical materials include membranes, tubes, pouches and clumps. One particular example of an application of this medical material is an alternative medical membrane, and more specifically, a preferable example is an alternative medical membrane having a crosslinked gelatin layer or hyaluronic acid layer on one or both of its sides. In this case, the thickness is preferably about 0.1–5 mm.

The gelatin gel layer that is able to be present on the surface of the alternative medical membrane of the present invention acts as an adhesion preventive layer for preventing invasion of cells from the surrounding body tissue at locations requiring prevention of adhesion due to the action of gelatin that impairs cell adhesion and growth. In addition, hyaluronic acid has the effect of improving stability of collagen as well as the effect of preventing adhesion. In the alternative medical membrane of the present invention, since it is necessary for the gelatin gel layer or hyaluronic acid layer to remain without being degraded or absorbed for about 3–4 weeks after applying to the body, crosslinking treatment is performed to this gelatin gel layer or hyaluronic acid layer.

In order to prepare the collagen material of the present invention, an approximately 1 N hydrochloric acid solution (pH of about 3) of extracted collagen as described above (and naturally following purification) is prepared (in the form of a solution of non-fibrous collagen in which collagen molecules are dispersed in the form of monomers and oligomers, and to apply similarly hereinafter; collagen concentration being preferably about 0.5–3 wt %, and particularly preferably about 1 wt %), and a collagen hydrochloric acid solution layer is formed in a container such as a Petri dish so that the liquid layer has an arbitrary uniform thickness using any routine method such as pouring. In the case of seeking a tubular material, for example, a mold in which a portion corresponding to the wall portion of said tubular material is hollow should be used, and depending on the case, this layer should be formed by coating and air-drying and so forth onto the surface of a base material such as a mandrel. In the case of using a material other than collagen such as polyglycolic acid and so forth that can be a substance having biocompatibility and can be degraded and absorbed in the body (for use as a material contained inside a collagen matrix), a sheet-like or tubular mesh-like material of said material itself should be contained inside said collagen hydrochloric acid solution layer. In the case of using such a material for the matrix (non-woven fabric-like sheet or tube), collagen such as amorphous collagen or fibrous collagen (or hyaluronic acid and so forth depending on the case) should be filled into said matrix (such as by allowing to seep in under reduced pressure). Furthermore, in the following explanation, the explanation of filling collagen and so forth into a matrix, further processing performed on said filled collagen, and further processing performed on the matrix treated in this manner, unless specified otherwise, apply to the case of a non-collagen material in which a substance having biocompatibility that is degraded and absorbed in the body is used for the matrix, and collagen and so forth is filled into said matrix. Although the thickness of the collagen hydrochloric acid solution layer is determined according to the application of the collagen material of the present invention, in the case of using, for example, as an alternative medical membrane for an endocranium, the thickness is preferably about 1–5 cm, and particularly preferably about 1–3 cm. This is then frozen preferably at about −10 to −196° C., and particularly preferably at about −20° C., for at least about 6 hours, preferably about 6–48 hours, and particularly preferably about 24 hours. As a result of freezing, fine pieces of ice are formed between the collagen molecules dispersed in the hydrochloric acid solution, and phase separation occurs in the collagen hydrochloric acid solution resulting in the formation of ultra-fine fibers due to rearrangement of the collagen molecules. If the freezing time is less than 6 hours, since the collagen hydrochloric acid solution is not adequately frozen, there is insufficient formation of ultra-fine fibers of the collagen molecules, thereby preventing from obtaining adequate physical properties. Next, the above-mentioned frozen collagen hydrochloric acid solution is freeze-dried in a vacuum preferably at about −40 to −80°

C., and particularly preferably at about −80° C., preferably for about 24–48 hours, and particularly preferably for about 48 hours. As a result of freeze-drying, together with the fine pieces of ice between the collagen molecules being vaporized, the ultra-fine fibers comprised of collagen molecules serve as the basic units to obtain a non-woven fabric-like collagen structure pluralistically composed of fine fibers, narrow fibers, fibers and plate-like fibers as previously described. Furthermore, this procedure consisting of freezing, (storing) and freeze-drying performed on this collagen hydrochloric acid solution is an essential procedure in the case of seeking fibrous collagen even in the case of a collagen material that also uses a non-collagen material such as polyglycolic acid etc.

Next, non-fibrous collagen, which can be a substance that has biocompatibility and can be degraded and absorbed in the body, and more specifically, a hydrochloric acid solution of extracted collagen, is introduced into the matrix of the non-woven fabric-like collagen structure obtained above (this procedure is not required as a general rule in the case of using polyglycolic acid and so forth as the material that can be a substance having biocompatibility that can be degraded and absorbed in the body (in the form of a material that is contained inside the collagen matrix)). Here, the collagen concentration of said solution is preferably 0.5 wt % or less. This is because said introduction proceeds smoothly and dispersion of said introduced solution in said matrix is more uniform, resulting in the removal of residual air in said matrix being carried out smoothly. As a specific example of simple methods for introducing said solution, said collagen hydrochloric acid solution is aspirated with a weak vacuum of about 50 cm $H_2O$ using, for example, an aspirator, since said matrix does not have a large resistance. Naturally, other methods may also be used, such as a method in which said collagen hydrochloric acid solution is allowed to seep into said matrix naturally by using the vacuum atmosphere in the previous freeze-drying procedure. Furthermore, in order to prevent the collagen fibers in said matrix formed in the previous procedure from being dissolved by said collagen hydrochloric acid solution (which naturally also contains water), it is preferable to perform thermal dehydration crosslinking on said non-woven fabric-like collagen layer prior to introducing said collagen hydrochloric acid solution. Said matrix is preferably heated in a vacuum preferably at about 105–150° C., and particularly preferably at about 140° C., preferably for about 6–48 hours, and particularly preferably about 24 hours. Here, if the heating temperature is below about 105° C., adequate crosslinking does not occur, while if the heating temperature exceeds about 150° C., the collagen ends up degenerating. Furthermore, the inherent objective of this procedure is to regulate the collagen material of the present invention to remain for a desired period of time after applying a medical material containing the collagen material of the present invention to the body.

Next, the non-woven fabric-like collagen structure in which collagen hydrochloric acid solution has been introduced into the matrix is temporarily frozen, and after holding that state for a predetermined amount of time, is freeze-dried to convert said introduced collagen hydrochloric acid solution into fibrous collagen. As a result, the predetermined space of the cavities of said matrix is filled with newly formed collagen. Namely, the cavities in said matrix are filled with said newly formed collagen such that said newly formed collagen intertwines with the fibrous collagen that composes said matrix. Furthermore, the conditions for this are the same as that of the freezing and freeze-drying processes described above. This procedure is not required as a general rule in the case of using polyglycolic acid and so forth as the material that can be a substance having biocompatibility that is able to be degraded and absorbed in the body (in the form of a material contained inside the collagen matrix)). Next, thermal dehydration crosslinking (the conditions of which are the same as the thermal dehydration crosslinking previously described) is performed after pressing said matrix, in which the predetermined space of the cavities is filled with said newly formed collagen (at, for example, 500 $kgf/cm^2$ for 15 seconds).

The collagen material of the present invention produced in the manner described above has, in the dry state, one-point support tensile force of at least 30 N and rupture resistance tensile force of at least 65 N, and in the wet state, one-point support tensile force of at least 1.4 N and rupture resistance tensile force of at least 6.5 N (in the case of a collagen material having a thickness of 1 mm and collagen fibers in which a substance having biocompatibility that is able to be degraded and absorbed in the body (to be referred to as a biodegradable, absorbable substance) that is filled into the matrix contains newly formed collagen ultra-fine fibers (to be referred to as filled collagen fibers) in the matrix). Alternatively, the collagen material of the present invention produced in the manner described above has, in the dry state, one-point support tensile force of at least 10 N and rupture resistance tensile force of at least 25 N, and in the wet state, one-point support tensile force of at least 5 N and rupture resistance tensile force of at least 15 N (in the case of a collagen material having a thickness of 1 mm and using polyglycolic acid and so forth for the biodegradable, absorbable substance contained inside the matrix, with capabilities naturally exceeding the above values in the case of using a non-collagen material for said matrix). Since this collagen material has superior strength in comparing with collagen materials of the prior art, it can be processed into various types of medical materials and can also be sutured. (In the latter collagen material in particular, since strength is superior in the wet state, it is favorable because it can be used regardless of the level of skill of suturing technique of the surgeon.) In addition, it is able to retain its shape for about 3–8 weeks in the case of being applied in the body. Moreover, it also retains the inherent properties of collagen as a medical material.

Furthermore, in the case of desiring even greater strength, this procedure of introducing said collagen hydrochloric acid solution into said matrix (under the same conditions as described above), freezing and freeze-drying (under the same conditions as described above) may be repeated at least once (normally repeating once is sufficient).

Although the collagen material of the present invention can be obtained for the most part with the steps described above, a non-fibrous collagen layer may be formed at a predetermined site on the surface of the above collagen material as necessary. The following provides a description of a specific method for accomplishing this.

(1) Said pressed collagen material is immersed in a hydrochloric acid solution of extracted collagen (collagen concentration: about 0.5–3 wt %, and particularly 2 wt %) and air-dried (and this is performed at least once, although one time is sufficient in ordinary applications).

(2) Next, thermal dehydration crosslinking is performed on the collagen material having a non-fibrous collagen layer at the predetermined site on said surface (and this can be performed under the same conditions as previously described).

Here, the collagen material having a non-fibrous collagen layer at a predetermined site on said surface may be additionally pressed between the above steps (1) and (2). This is because the surface of the collagen material ultimately obtained has fewer irregularities as well as improved "feeling" and "texture".

Furthermore, although the explanation thus far has focused on the use of the one which is formed by using a collagen hydrochloric acid solution as a raw material and newly forming collagen fibers therein after introducing said solution into said matrix, as the substance which is filled into the above matrix, has biocompatibility and is able to be degraded and absorbed in the body, depending on the particular application, said substance may be the one which is formed by performing simply air-drying after introducing, for example, said solution or a solution of hyaluronic acid into said matrix. The objective of the use of the one which is formed by performing simply air-drying following their introduction as said substance to be filled is to suppress decrease in strength in the wet state due to further infiltration into the cavities by body fluids during application of medical materials comprising the collagen material of the present invention to the body, by eliminating said cavities. The procedure following introduction of said solution into said matrix and air-drying should only consist of the application of thermal dehydration crosslinking as a general rule (provided that this procedure is performed while applying pressure of 200 kgf/cm$^2$), or, depending on the case, pressing and additional step (1) described above should be performed prior to application of thermal dehydration crosslinking.

Moreover, the collagen material obtained with the above basic steps or the above basic steps plus the above additional steps may be sterilized as necessary by ethylene oxide gas treatment, ultraviolet irradiation or gamma ray irradiation and so forth.

In the case of processing the collagen material of the present invention prepared in the manner described above into an alternative medical membrane having a crosslinked gelatin layer or hyaluronic acid layer on one or both of its sides, in the case of a gelatin gel layer, the gelatin gel layer is formed by using an aqueous gelatin solution of preferably about 2–70 wt % and particularly preferably about 60 wt %. In the case of using an aqueous gelatin solution of about 60 wt %, the gelatin gel layer is formed to a thickness of preferably about 0.1–5 mm and particularly preferably about 1 mm in the wet state, or preferably about 0.06–3 mm and particularly preferably about 0.6 mm in the dry state. Although the gelatin gel layer, may be formed by a method such as coating or immersion, for example, the aqueous gelatin solution may be poured into a container such as a Petri dish to the required thickness, and the collagen material of the present invention obtained in the manner described above may be placed on top of it and allowed to stand to allow the gelatin to gelatinize. In the case of forming a gelatin gel layer on both sides, a similar process is performed on the other side as well to form gelatin gel layers on both sides.

Next, the collagen material on which a gelatin gel layer has been formed on one or both sides obtained in this manner is subjected to crosslinking treatment. As a result of performing this crosslinking treatment, the rate of degradation and absorption of the gelatin gel layer is controlled. Thermal dehydration crosslinking is preferable for the crosslinking method. In order to allow the gelatin gel layer to remain for about 3–4 weeks after application to the body, the collagen material on which said gelatin gel layer has been formed is subjected to thermal dehydration crosslinking treatment in a vacuum preferably at about 105–150° C. and particularly preferably about 140° C. for preferably about 6–48 hours and particularly preferably about 24 hours. If the temperature is below about 105° C., the crosslinking reaction does not occur adequately, and if the temperature exceeds 150° C., the collagen ends up denaturing.

The crosslinked gelatin gel layer formed in this manner has the role of preventing the collagen portion of the present alternative medical membrane from adhering to surrounding tissue until each biomembrane is regenerated, and the gelatin gel layer remains without being degraded or absorbed for about 3–4 weeks until the biomembrane extends and regenerates from around the membrane missing portion and fills in the missing portion of the membrane.

On the other hand, in the case of forming a hyaluronic acid layer, an aqueous sodium hyaluronate solution layer is formed by a method such as coating or immersion on one or both sides of the collagen material of the present invention obtained in the manner described above by using an aqueous sodium hyaluronate solution of preferably about 0.5–2.0 mg/ml and particularly preferably about 1.0 mg/ml, after which this aqueous solution layer is air-dried to form a hyaluronic acid layer. The aqueous sodium hyaluronate solution layer is formed to a thickness of preferably about 0.5–4.0 mm and particularly preferably about 2 mm in the wet state, or preferably about 0.1–2.0 mm and particularly preferably about 1.0 mm in the dry state (in the case of an aqueous solution of about 1.0 mg/ml) so that the hyaluronic acid layer is able to remain without being degraded or absorbed for about 3–4 weeks until the biomembrane extends and is regenerated from around the missing portion of the membrane to be repaired and fills in the missing portion of the membrane. In order to fix the hyaluronic acid on the surface of the collage material and form the hyaluronic acid layer, a second crosslinking treatment is performed. In the case of hyaluronic acid, it is preferable to perform crosslinking treatment with water-soluble carbodiimide (WSC). In this case, it is preferable to premix WSC with aqueous sodium hyaluronate solution and apply to the collagen material together with sodium hyaluronate to crosslink the carboxyl groups of the collagen with the amino groups of the hyaluronic acid. The concentration of WSC contained in aqueous sodium hyaluronate solution is preferably about 5–20 mg/ml and particularly preferably about 8–15 mg/ml. An aqueous solution containing this sodium hyaluronate and WSC is prepared, stirred well and coated onto one or both sides of the collagen material preferably to a thickness of about 1 mm followed by air-drying to form the hyaluronic acid layer.

Since the collagen material of the present invention has excellent strength, it can also be used as surgical suture. A thread-like material containing the collagen material of the present invention can be prepared by substituting the first step of the preparing method described above with the following one, i.e., by preparing an about 1 N hydrochloric acid solution (pH of about 3) of extracted (and naturally, purified) collagen (the collagen concentration is preferably about 0.5–3 wt % and particularly preferably about 1 wt %), and wet spinning by having this jetted out into a coagulation bath through a nozzle having an aperture of preferably about 50–300 μm and particularly preferably about 100 μm, and the other steps are performed in the same manner as the preparation method of the collagen material described above.

Since the collagen material of the present invention prepared in the manner described above has superior physical properties, and particularly superior tear strength, in compared with extracted collagen materials of the prior art, it can be processed into various medical materials using the collagen material alone without laminating to synthetic polymer materials and so forth, and can also suture. In addition, in the case of applying the collagen material of the present invention in the body, it is able to retain its shape for about 3–8 weeks without immediately dissolving. For these reasons, by processing the collagen material of the present invention into the form of a membrane, tube, pouch or clump according to the particular application, it can be used as various types of medical materials. For example, it can be used as an artificial tube for nerve, artificial tube for spinal cord, artificial esophagus, artificial trachea, artificial blood vessel, artificial valve, artificial alternative medical membrane such as alternative endocranium, artificial ligamenta, artificial tendon, surgical suture, surgical prostheses, surgical reinforcement, wound protecting material, artificial skin and artificial cornea, and can accelerate recovery and regeneration of injured body tissue. Alternatively, it can also be used as a material for astriction or three-dimensional medium in cell culturing.

In addition, an alternative medical membrane comprising the medical material of the present invention obtained in the manner described above can be used to prevent adhesion of viscera and surrounding tissue in missing portions of membrane by filling said portions following various types of surgery. In the alternative medical membrane of the present invention, it is used in which a gelatin gel layer or hyaluronic acid layer is formed on one or both sides so that the crosslinked gelatin gel layer or hyaluronic acid layer is facing the side that comes in contact with surrounding tissue for which it is necessary to prevent adhesion. In the case of using the present alternative medical membrane as an alternative membrane of the pericardium, it is used in which a gelatin gel layer or hyaluronic acid layer is formed on both sides so that the gelatin gel layer or hyaluronic acid layer is facing the sides that come in contact with the surrounding tissue, while in the case of using the present alternative medical membrane as an alternative membrane of the pleura, peritoneum or serous membrane, it is used in which a gelatin gel layer or hyaluronic acid layer is formed on one side so that the gelatin gel layer or hyaluronic acid layer is facing the side that comes in contact with the surrounding tissue. In the case of using as an alternative membrane of the endocranium, it can be used in which a gelatin gel layer or hyaluronic acid layer is formed on either one or both sides. In the case of using an alternative membrane in which a gelatin gel layer or hyaluronic acid layer is formed on one side, it is used so that the gelatin gel layer or hyaluronic acid layer is facing the side that comes in contact with brain parenchymal tissue. Moreover, this alternative membrane material can also be used as reinforcement for suturing blood vessels, digestive tract, trachea, ureter, urinary bladder, serous membrane or periodontal membrane.

The alternative medical membrane of the present invention that serves as a material for filling missing portions of biomembranes in the manner described above can be used as an alternative membrane of the endocranium, pericardium, pleura, peritoneum or serous membrane. When the present alternative membrane is applied to a surgical wound, while the biomembrane such as the endocranium, pericardium, pleura, peritoneum or serous membrane that remains around the surgical wound extends and regenerates from the site in contact with the present alternative membrane by using the collagen portion of the present alternative membrane as a foothold for regeneration, adhesion is prevented at sites where body tissue comes in contact with the gelatin gel layer or hyaluronic acid layer to prevent cell invasion and extension so that ultimately, the missing portion is filled in by the regenerated biomembrane, after which the present alternative membrane is completely eliminated as a result of degradation and absorption by the body.

As described above, although the collagen material of the present invention as well as a medical material containing the collagen material of the present invention, and particularly an alternative medical membrane, have tear strength that is superior in comparing with conventional collagen materials and medical materials in which they are contained, when using the present medical material as, for example, an artificial urinary bladder, there are cases in which even greater strength is required. Consequently, the collagen material of the present invention and a medical material containing the collagen material of the present invention may have, when so required, a sheet-like mesh intermediate comprised of a biodegradable, absorbable material inside. Examples of said biodegradable, absorbable materials include polyglycolic acid, polylactic acid, copolymer of glycolic acid and lactic acid, polydioxanone, copolymer of glycolic acid and trimethylene carbonate, or a mixture of polyglycolic acid and polylactic acid. Sheet-like mesh intermediates composed of these materials are in the form of, for example, a mesh sheet, woven fabric, non-woven fabric or sheet containing punched holes having a hole diameter of, for example, about 50–2000 μm. Although their thickness is, for example, about 100–2000 μm, the hole diameter and thickness of the mesh intermediate should be suitably changed according to the specific application.

In order to prepare a collagen material having a sheet-like mesh intermediate composed of a biodegradable, absorbable material inside a matrix, the sheet-like mesh intermediate as described above is left immersed in a collagen hydrochloric acid solution cast during formation of the collagen hydrochloric acid solution as the first step of the preparation method for the collagen material previously described, after which the collagen hydrochloric acid solution layer is subjected to following steps such as freezing and freeze-drying. However, in the case of this form, since it is generally unnecessary to fill the matrix with new collagen ultra-fine fibers, the steps required for said filling, for example the steps consisting of additional introduction of extracted collagen hydrochloric acid solution, repeated freezing and repeated freeze-drying, as well as the final thermal dehydration crosslinking step, need not be performed. On the other hand, other additional steps, namely formation of additional layers on the surface of said collagen material (on one or both sides), such as, for example, the formation of a collagen solution layer, gelatin gel layer or hyaluronic acid layer (and thermal dehydration crosslinking is performed after these procedures as a general rule), may be suitably performed as necessary.

The following provides an explanation of the present invention using an example of producing a membrane-like collagen material.

EXAMPLE 1

A 1 N hydrochloric acid solution of extracted collagen (collagen concentration: 1 wt %) was prepared using pigskin collagen, and the solution was poured into a Petri dish to prepare a collagen solution layer having a thickness of 18 mm. This was then frozen for 24 hours at −20° C. and then freeze-dried for 48 hours at −80° C. Next, a multi-element structure of said freeze-dried collagen fibers (to be simply referred to as the multi-element structure) was subjected to thermal dehydration crosslinking for 24 hours at 140° C. under a vacuum followed by generating negative pressure (50 cmH$_2$O) inside said multi-element structure with a flow aspirator to introduce a 1 N hydrochloric acid solution of extracted collagen (collagen concentration: 0.5 wt %) into said multi-element structure and fill the cavities inside said multi-element structure with non-fibrous collagen. Next, after performing freezing and freeze-drying under the same conditions as previously described (procedure for reducing the cavities inside said multi-element structure by newly formed fibrous collagen), said multi-element structure was compressed (500 kgf/cm$^2$) to a thickness of 1 mm followed by immersion of said compressed multi-element structure in a 1 N hydrochloric acid solution of extracted collagen (collagen concentration: 2 wt %) and air-drying (formation of collagen solution layer; performed once). This was then subjected to thermal dehydration crosslinking under the same conditions as previously described to obtain the collagen material of the present invention.

The one-point support tensile force and rupture resistance tensile force were measured in the wet and dry states for the collagen material of the present invention prepared in the manner described above according to the methods described below. The results are shown in Table 1.

Test strips of 10 mm×25 mm were prepared for measuring the above items. Tensile force was applied uniformly at speed B (5 mm/min) of ISO in the measure axis direction of the test strip using a digital push-pull gauge (CPU gauge from Aiko Engineering Co., Ltd.) in a constant temperature, constant humidity bath at 25° C. and humidity of 50% according to the method described below, and the maximum tensile force at which the membrane ruptures was measured in both the dry and wet states (hydrated for 1 minute or 30 minutes in physiological saline at 37° C.).

1. One-Point Support Tensile Force

A site 5 mm to the inside from the center of one end of a test strip was sutured with a thread (4-0 proline or 2 dexon) and anchored, while tensile force was applied to the other end by uniformly clamping with a clip.

2. Rupture Resistance Tensile Force

Tensile force was applied to both ends of a test strip by uniformly clamping both ends with clips.

The results are shown in Table 1 (in the table, "Wet State A" indicates data for which the hydration time was 1 minute, while "Wet State B" indicates data for which the hydration time was 30 minutes).

EXAMPLE 2

With the exception of performing the procedure for forming a collagen solution layer onto the above compressed multi-element structure five times, a collagen material of the present invention was obtained in the same manner as Example 1. The one-point support tensile force and rupture resistance tensile force of said collagen material was measured in the dry and wet states according to the same method as Example 1. Those results are shown in Table 1.

EXAMPLE 3

With the exception of performing thermal dehydration crosslinking treatment under the same conditions as previously described and reducing the cavities inside the multi-element structure with newly formed fibrous collagen in order between the above second freeze-drying procedure and compression procedure, as well as not performing the procedure for forming a collagen solution layer on the above compressed multi-element structure, the one-point support tensile force and rupture resistance tensile force of the resulting collagen material of the present invention were measured in the dry and wet states according to the same method as Example 1. Those results are shown in Table 1.

EXAMPLE 4

With the exception of not performing the procedure for forming a collagen solution layer on the above compressed multi-element structure, a collagen material of the present invention was obtained in the same manner as Example 1. The one-point support tensile force and rupture resistance tensile force of said collagen material were measured in the dry and wet states according to the same method as Example 1. Those results are shown in Table 1.

EXAMPLE 5

With the exception of containing a mesh sheet (aperture: 1 mm) of polyglycolic acid inside the collagen solution layer formed first, the surface of which was pretreated with plasma discharge treatment, during formation of said first collagen solution layer, and not performing the procedure for reducing the cavities inside said multi-element structure with newly formed fibrous collagen, a collagen material of the present invention was obtained in the same manner as Example 1. The one-point support tensile force and rupture resistance tensile force of said collagen material were measured in the dry and wet states according to the same method as Example 1. Those results are shown in Table 1.

EXAMPLE 6

With the exception of performing a procedure for forming a gelatin gel layer on one side of the above compressed multi-element structure (by coating a 15% aqueous gelatin solution onto said side and drying) instead of forming a collagen solution layer on said compressed multi-element structure, a collagen material of the present invention was obtained in the same manner as Example 5. The one-point support tensile force and rupture resistance tensile force of said collagen material were measured in the dry and wet states according to the same method as Example 1. Those results are shown in Table 1.

EXAMPLE 7

With the exception of performing the procedure for forming a gelatin gel layer on both sides of the above compressed multi-element structure, a collagen material of the present invention was obtained in the same manner as Example 6. The one-point support tensile force and rupture resistance tensile force of said collagen material were measured in the dry and wet states according to the same method as Example 1. Those results are shown in Table 1.

TABLE 1

|  | Dry State | | Wet State A | | Wet State B | (Units: N) |
| --- | --- | --- | --- | --- | --- | --- |
|  | One-point support tensile force | Rupture resistance tensile force | One-point support tensile force | Rupture resistance tensile force | One-point support tensile force | Rupture resistance tensile force |
| Example 1 | 50.9 | 124.8 | 11.2 | 44.3 | 1.6 | — |
| Example 2 | 54.6 | 114.6 | 19.6 | 23.4 | 2.0 | — |
| Example 3 | 44.3 | 91.4 | 5.1 | 12.1 | 2.5 | — |
| Example 4 | 33.1 | 68.3 | 1.4 | 6.5 | 1.2 | 4.1 |
| Example 5 | 11.1 | 27.9 | 5.6 | 18.8 | — | — |
| Example 6 | 18.0 | 45.6 | 12.9 | 20.0 | — | — |
| Example 7 | 20.0 | 49.8 | 16.5 | 34.2 | — | — |
| Reference | 1.0 | 3.1 | 0.7 | 2.6 | — | — |

As shown in Table 1, the collagen materials of the present invention were confirmed to have superior physical properties that are able to withstand suturing. Furthermore, the reference data in the table shows the data for a mesh sheet of polyglycolic acid only.

EXAMPLE 8

A non-woven fabric (2 plies, thickness: 0.20 mm, percentage of void: 88.75%) of polyglycolic acid subjected to plasma discharge treatment and extracted collagen hydrochloric acid solution (collagen concentration: 1 wt %) in an amount sufficient to allow immersion of the above non-woven fabric were placed in a container, said container was housed in a desiccator, and the pressure inside said desiccator was reduced with a flow aspirator (−50 cmH$_2$O). After then maintaining that state for a predetermined amount of time (1–2 minutes) and allowing said extracted collagen hydrochloric acid solution to adequately soak into said non-woven fabric, said non-woven fabric was removed from said desiccator and air-dried. After performing each of the procedures of freezing, holding that state, freeze-drying and thermal dehydration crosslinking under the same conditions as Example 1 on said air-dried non-woven fabric, immersion in extracted collagen hydrochloric acid solution (collagen concentration: 1 wt %) and air-drying were repeated twice to form a solution layer of amorphous collagen on the surface of the non-woven fabric filled with fibrous collagen. Next, after forming a gelatin gel layer on the surface of said amorphous collagen solution layer (performed by repeating immersion in 20% aqueous gelatin solution and air-drying twice), thermal dehydration crosslinking was performed under the same conditions as Example 1 to obtain a collagen material of the present invention.

EXAMPLE 9

With the exception of using that having 4 plies (thickness: 0.55 mm, percentage of void: 75.1%) for the non-woven fabric of polyglycolic acid and not performing the series of procedures consisting of freezing, holding that state, freeze-drying and thermal dehydration crosslinking on said non-woven fabric into which extracted collagen hydrochloric acid solution was allowed to adequately soak, a collagen material of the present invention was obtained in the same manner as Example 8. Furthermore, since the obtaining of strength was able to be confirmed in a preliminary test, additional detailed strength testing was not performed in the same manner as Example 8.

INDUSTRIAL APPLICABILITY

Since the collagen material of the present invention has physical properties that allow suturing even though it retains biochemical properties inherently possessed by collagen, it can be widely used as various types of medical materials. In addition, the alternative medical membrane of the present invention presents no ethical problems, can be provided in stable supply, and can be sutured to a surgical wound as a material that fills in the missing portion of a biomembrane or as a material that prevents adhesion. In addition, while it demonstrates effects that prevent adhesion, since it remains for a period of time after suturing until the biomembrane regenerates and is then gradually degraded and absorbed, it does not cause inflammation and so forth as a result of remaining in body tissue for a long period of time, thereby allowing it to be used safely.

The invention claimed is:

1. A collagen material consisting of a matrix of a non-woven fabric multi-element structure of collagen fibers having ultra-fine fibers of collagen as its basic unit,
    the matrix being filled with a substance having biocompatibility that can be degraded and absorbed in the body,
    wherein said substance having biocompatibility that can be degraded and absorbed in the body is fibrous collagen fiber or a substance selected from the group consisting of polyglycolic acid, polylactic acid, copolymer of glycolic acid and lactic acid, polydioxanone, copolymer of glycolic acid and trimethylene carbonate, and a mixture of polyglycolic acid and polylactic acid,
    wherein said non-woven fabric multi-element structure of collagen fibers is composed of collagen plate fibers having a diameter of 20–50 μm randomly intertwined,
    said plate fibers consisting of collagen fibers having a diameter of 5–8 μm, wherein the collagen fibers overlap in the coaxial direction,
    said fibers consisting of bundled rows of narrow collagen fibers having a diameter of 1–3 μm alternately overlapping as warp and weft,
    said narrow fibers consisting of bundled fine collagen fibers having a diameter of 30–70 nm, and
    said fine fibers consisting of ultra-fine collagen fibers having a diameter of 3–7 nm that are comprised of several bundled collagen molecules.

2. The collagen material according to claim 1, wherein said substance having biocompatibility that can be degraded and absorbed in the body and being filled into said matrix is fibrous collagen fiber containing ultra-fine fibers of collagen newly formed by performing a freezing and freeze-drying procedure to a hydrochloric acid solution of extracted collagen introduced into said matrix.

3. The collagen material according to claim 1, wherein said substance having biocompatibility that can be degraded and absorbed in the body and being filled into said matrix is selected from the group consisting of polyglycolic acid, polylactic acid, copolymer of glycolic acid and lactic acid, polydioxanone, copolymer of glycolic acid and trimethylene carbonate, and a mixture of polyglycolic acid and polylactic acid, and is used as a mesh sheet or tube, or a non-woven fabric sheet or tube.

4. A collagen material according to claim 1 in which the collagen fiber containing ultra-fine fibers of collagen is formed by performing a freezing, freeze-drying and thermal dehydration crosslinking procedure to a hydrochloric acid solution of extracted collagen.

5. The collagen material according to claim 4, wherein said collagen fibers are composed of collagen plate fibers having a diameter of 20–50 μm are randomly intertwined, said plate fibers are composed of collagen fibers having a diameter of 5–8 μm overlap in the coaxial direction, said fibers are composed of bundled rows of narrow collagen fibers having a diameter of 1–3 μm are alternately overlapping as warp and weft, said narrow fibers are composed of fine collagen fibers having a diameter of 30–70 nm are bundled, and said fine fibers are composed of ultra-fine collagen fibers having a diameter of 3–7 nm that are comprised of several collagen molecules are bundled.

6. The collagen material according to claim 2, where said collagen material has one-point support tensile force of at least 30 N and rupture resistance tensile force of at least 65 N in the dry state, and has one-point support tensile force of at least 1.4 N and rupture resistance tensile force of at least 6.5 N in the wet state for a thickness of 1 mm.

7. The collagen material according to any one of claims 3, 4 or 5, wherein said collagen material has one-point support tensile force of at least 10 N and rupture resistance tensile force of at least 25 N in the dry state, and has one-point support tensile force of at least 5 N and rupture resistance tensile force of at least 15 N in the wet state for a thickness of 1 mm.

8. A process for producing the collagen material according to claim 1, comprising performing at least the steps indicated below in order:
  a. collagen solution layer is formed by casting a hydrochloric acid solution of extracted collagen to a desired thickness;
  b. said collagen solution layer is temporarily frozen and held in that static for a desired amount of time followed by freeze-drying;
  c. thermal dehydration crosslinking is performed for a predetermined amount of time on said freeze-dried product;
  d. said hydrochloric acid solution of extracted collagen is introduced into the matrix of said thermal dehydration crosslinked product;
  e. the product introduced said solution of extracted collagen therein is temporarily frozen, held in that state for a predetermined amount of time and then freeze-dried;
  g. said freeze-dried product is compressed; and,
  i. thermal dehydration crosslinking is performed for a predetermined amount of time on that compressed product.

9. The process according to claim 8, wherein the following steps are performed in order between said step e and step g:
  f1. said hydrochloric acid solution of extracted collagen is again introduced in the matrix of said freeze-dried product; and,
  f2. the product introduced said extracted collagen solution therein is temporarily frozen, held in that state for a desired amount of time, and then freeze-dried.

10. The process according to claim 8 or 9, wherein the following step is performed between said steps g and i:
  h1. a collagen solution layer is formed at a predetermined site on the surface of said compressed product.

11. The process according to claim 10, wherein the following step is performed between said steps h1 and i:
  h2. said collagen solution layer is compressed.

12. The process according to claim 8 or 9, wherein the freezing and holding time during the freezing procedure in said steps b, e and f2 is 6–48 hours.

13. The process according to claim 8 or 9, wherein the collagen concentration of the hydrochloric acid solution of extracted collagen in said steps d and f1 is 0.5 wt % or less.

14. The process according to claim 10, wherein the collagen concentration of the hydrochloric acid solution of extracted collagen for forming a collagen solution layer in said step h1 is 2.0 wt % or less.

15. The process according to claim 8 or 12, wherein casting of a hydrochloric acid solution of extracted collagen in said step a is divided into two procedures, and a mesh-like sheet or tube comprising a material selected from the group consisting of polyglycolic acid, polylactic acid, copolymer of glycolic acid and lactic acid, polydioxanone, copolymer of glycolic acid and trimethylene carbonate and a mixture of polyglycolic acid and polylactic acid is contained between both collagen solution layers between both casting procedures, said step g is performed after said step c while said step i is not performed.

16. The process according to claim 15, wherein the following steps are additionally performed after said step g:
  h3. a collagen solution layer or gelatin gel layer is formed on at least one side of said compressed product; and,
  h4. thermal dehydration crosslinking is performed on the product formed said collagen solution layer or said gelatin gel layer.

17. The process according to claim 16, wherein the collagen concentration of the hydrochloric acid solution of extracted collagen for forming said collagen solution layer is 2 wt % or less.

18. The process according to claim 16, wherein said gelatin concentration of the gelatin aqueous solution for forming said gelatin gel layer is 5–25 wt %.

19. A process for producing the collagen material according to claim 1, comprising performing at least the following steps in order:
  j. a hydrochloric acid solution of extracted collagen is introduced into a non-woven fabric-like sheet-like or tube-like matrix comprising a material selected from the group consisting of polyglycolic acid, polylactic acid, copolymer of glycolic acid and lactic acid, polydioxanone, copolymer of glycolic acid and trimethylene carbonate and a mixture of polyglycolic acid and polylactic acid, followed by air-drying;
  l. a collagen solution layer is formed on at least one side of the product introduced and air-dried said hydrochloric acid solution of extracted collagen;
  o. a gelatin layer is formed on said collagen solution layer; and,
  p. thermal dehydration crosslinking is performed on the product formed said gelatin layer for predetermined amount of time.

20. The process according to claim 19, wherein the following step k is performed between said steps j and l, and the following step m is performed between said steps l and o:
  k. the product introduced said extracted collagen is temporarily frozen, and that state is maintained for a predetermined amount of time followed by freeze-drying;
  m1. the product on which said collagen solution layer is formed is temporarily frozen, and that state is maintained for a predetermined amount of time followed by freeze-drying; and,
  m2. the product freeze-dried is compressed.

21. The process according to claim 19 or 20, wherein the following step n is performed between said steps l and o or between said steps m2 and o:
  n. thermal dehydration crosslinking is performed for a predetermined amount of time on the product on which said collagen solution layer is formed or the product freeze-dried.

22. The process according to claim 19 or 20, wherein the collagen concentration of the hydrochloric acid solution of extracted collagen in said steps j and l is 2.0 wt % or less.

23. The process according to claim 19 or 20, wherein the gelatin concentration of the gelatin aqueous solution in said step o is 5–25 wt %.

24. The process according to claim 8 or 9, wherein the collagen material produced has one-point support tensile force of at least 30 N and rupture resistance tensile force of at least 65 N in the dry state, and one-point support tensile force of at least 1.4 N and rupture resistance tensile force of at least 6.5 N in the wet state for a thickness of 1 mm.

25. The process according to claim 15, wherein the collagen material produced has one-point support tensile force of at least 10 N and rupture resistance tensile force of at least 25 N in the dry state, and one-point support tensile force of at least 5 N and rupture resistance tensile force of at least 25 N in the wet state for a thickness of 1 mm.

* * * * *